(12) United States Patent
Govari et al.

(10) Patent No.: US 10,327,734 B2
(45) Date of Patent: Jun. 25, 2019

(54) MEASUREMENT OF TISSUE THICKNESS USING ULTRASOUND AND FORCE MEASUREMENTS

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US); Andres Claudio Altmann, Haifa (IL); Yaron Ephrath, Karkur (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 955 days.

(21) Appl. No.: 14/585,788

(22) Filed: Dec. 30, 2014

(65) Prior Publication Data
US 2016/0183915 A1    Jun. 30, 2016

(51) Int. Cl.
*A61B 8/12* (2006.01)
*A61B 5/00* (2006.01)
(Continued)

(52) U.S. Cl.
CPC .......... *A61B 8/429* (2013.01); *A61B 5/6852* (2013.01); *A61B 5/6885* (2013.01);
(Continued)

(58) Field of Classification Search
CPC ...................................................... A61B 8/12
See application file for complete search history.

(56) References Cited

U.S. PATENT DOCUMENTS 5,957,943 A * 9/1999 Vaitekunas ...... A61B 17/22012
604/22
6,226,542 B1    5/2001 Reisfeld
(Continued)

FOREIGN PATENT DOCUMENTS

EP        2 248 480 A1    11/2010
WO    WO 97/24981 A2     7/1997
(Continued)

OTHER PUBLICATIONS

"Ultrasound palpation sensor for tissue thickness and elasticity measurement—Assessment of transverse carpal ligament" by Y.P. Zheng et al. Ultrasonics. 44 (2006) e313-e317.*

(Continued)

*Primary Examiner* — Tse W Chen
*Assistant Examiner* — Jason M Ip
(74) *Attorney, Agent, or Firm* — Vincent J. Serrao

(57) ABSTRACT

Wall thickness of a cavity is determined by inserting a catheter into contact with a wall of a cavity in a body of a subject. The distal segment of the catheter is provided with a contact force sensor and an ultrasound transducer. The transducer is actuated to acquire ultrasound reflection data from the wall of the cavity, and while the transducer is actuated, the catheter is reciprocated against the wall of the cavity and the contact force measured between the catheter and the wall of the cavity. The reflection data is correlated with the contact force. A set of the correlated reflection data having the highest correlation with the contact force is identified. The tissue thickness between the inner surface and the identified set of the reflection data is calculated according to the time-of-flight therebetween.

16 Claims, 4 Drawing Sheets

(51) Int. Cl.
*A61B 8/00* (2006.01)
*A61B 8/08* (2006.01)
A61B 18/14 (2006.01)
A61B 17/22 (2006.01)
A61B 18/00 (2006.01)
A61B 90/00 (2016.01)

(52) U.S. Cl.
CPC .............. *A61B 8/0883* (2013.01); *A61B 8/12* (2013.01); *A61B 8/4254* (2013.01); *A61B 8/4263* (2013.01); *A61B 8/486* (2013.01); A61B 17/2202 (2013.01); A61B 18/1492 (2013.01); A61B 2018/00011 (2013.01); A61B 2018/00357 (2013.01); A61B 2018/00577 (2013.01); A61B 2018/00815 (2013.01); A61B 2018/00821 (2013.01); A61B 2018/00875 (2013.01); A61B 2090/061 (2016.02); A61B 2090/065 (2016.02); A61B 2090/374 (2016.02)

(56) References Cited

U.S. PATENT DOCUMENTS

| | | | |
|---|---|---|---|
| 6,301,496 B1 | 10/2001 | Reisfeld | |
| 6,494,840 B1* | 12/2002 | Mak | A61B 8/0858 600/443 |
| 6,554,774 B1 | 4/2003 | Miele | |
| 6,569,098 B2 | 5/2003 | Kawchuk | |
| 6,814,733 B2 | 11/2004 | Schwartz et al. | |
| 6,892,091 B1 | 5/2005 | Ben-Haim et al. | |
| 6,997,924 B2 | 2/2006 | Schwartz et al. | |
| 7,156,816 B2 | 1/2007 | Schwartz et al. | |
| 7,517,318 B2 | 4/2009 | Altmann et al. | |
| 7,536,218 B2 | 5/2009 | Govari et al. | |
| 7,578,789 B2* | 8/2009 | Sandrin | A61B 5/0048 600/438 |
| 7,604,601 B2 | 10/2009 | Altmann et al. | |
| 7,756,576 B2 | 7/2010 | Levin | |
| 7,877,128 B2 | 1/2011 | Schwartz | |
| 8,320,711 B2 | 11/2012 | Altmann et al. | |
| 8,583,220 B2 | 11/2013 | Schwartz | |
| 8,628,473 B2 | 1/2014 | Sliwa et al. | |
| 2005/0085728 A1 | 4/2005 | Fukuda | |
| 2012/0259194 A1 | 10/2012 | Selkee | |
| 2013/0123629 A1 | 5/2013 | Rosenberg et al. | |
| 2013/0190726 A1* | 7/2013 | Kesner | A61M 25/0105 604/510 |
| 2014/0094701 A1 | 4/2014 | Kwartowitz et al. | |
| 2014/0100563 A1 | 4/2014 | Govari et al. | |
| 2014/0142438 A1 | 5/2014 | Ludwin et al. | |

FOREIGN PATENT DOCUMENTS

WO WO 07/050960 A2 5/2007
WO WO 12/161880 A1 11/2012

OTHER PUBLICATIONS

European Search Report dated Jul. 1, 2016 from corresponding European Patent Application No. 15202371.9.
Kesner, Samuel B. et al., "Robotic catheter cardiac ablation combining ultrasound guidance and force control", The International Journal of Robotics Research, 2014, pp. 631-644, vol. 33(4).
Li, Xingfei et al., "A Portable Measurement Instrument for Soft Tissue Mechanical Properties", Instrumentation Science and Technology, 2004, pp. 611-626, vol. 32, No. 6.

\* cited by examiner

MEASUREMENT OF TISSUE THICKNESS USING ULTRASOUND AND FORCE MEASUREMENTS

BACKGROUND OF THE INVENTION

1. Field of the Invention

This invention relates to examination using ultrasonic waves. More particularly, this invention relates to analysis of contact between an ultrasonic probe and body tissue.

2. Description of the Related Art

Invasive and non-invasive ultrasound techniques have been used to assess tissues within the body. These techniques are particularly relevant to medical procedures in which is necessary to know the relationships of certain tissues to other tissues and to organs that are subject to injury from instruments such as ablation catheters, biopsy needles and the like. For example, cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

A known difficulty in the use of radiofrequency energy for cardiac tissue ablation is controlling local heating of tissue. There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects, coagulum, and or explosive steam pops due to overheating. If the radiofrequency device creates too large a lesion adjacent tissue can be inadvertently ablated. In some cases, perforation of the wall of the heart could occur. It is therefore desirable to know the thickness of the tissue being ablated.

U.S. Pat. No. 8,628,473 to Sliva et al, proposes an ablation catheter comprising an ablation element to ablate a biological member at a target region outside the catheter body and one or more acoustic transducers each configured to direct an acoustic beam toward a respective target ablation region and receive reflection echoes therefrom. The distal member includes a transducer housing in which the acoustic transducers are disposed, the transducer housing including at least one transducer window, which is the only portion in the distal member through which the acoustic beam passes. There is at least the at least one transducer window portion of the distal member.

U.S. Patent Application Publication No. 2013/0123629 by Rosenberg et al. describes a compressive body fat measuring techniques in which a force is applied to the tissue causing narrowing of the adipose tissue layer at the time of measuring. A bias in the adipose layer thickness measurement is dealt with, inter alia, by measuring changes in tissue impedance concurrently or intermittently with ultrasound measurement of adipose tissue layer thickness.

U.S. Patent Application Publication No. 2014/0142438 by Ludwin et al. describes a method, including pressing a distal end of a medical probe against a wall of a body cavity, and receiving from the probe first measurements of a force exerted by the distal end on the wall. The method also includes receiving from the probe second measurements indicating a displacement of the wall in response to the force. The method further includes estimating a thickness of the wall based on the first and the second measurements.

SUMMARY OF THE INVENTION

In embodiments of the invention, tissue thickness is measured using ultrasound, by determining the period for an ultrasound pulse from a transducer to be reflected back to the transducer (in the A-mode of operation of the transducer). As is illustrated in the figure, a catheter may be configured to measure tissue thickness by incorporating a transducer in the catheter distal tip; the transducer is placed in contact with the surface of the tissue. In practice, the measurement is difficult because within the signals acquired by the transducer the reflected pulses are difficult to distinguish from other background sound received by the transducer.

Embodiments of the present invention overcome this problem by placing the transducer in contact with the tissue, and moving the distal tip vertically, i.e., normal to the tissue surface, back and forth, thereby compressing are decompressing the tissue while the transducer operates. The vertical motion may be automatic, using, for example, a linear actuator incorporated into the distal tip. Alternatively the vertical motion may be manually produced by a user of the system or may naturally occur due to the contraction of the heart. The vertical motion causes the pulses to return at different periods, because of the differing distances of the tissue traversed by the pulses.

The distal tip also has a contact force sensor in the tip, and the force measured by the sensor varies as the tip moves. Embodiments of the invention correlate the measured contact force with the signals acquired by the transducer, in order to isolate pulses returning from a tissue interface of interest from background reflections and noise. The correlation may use the fact that the returning pulse period at a high force is less than the returning pulse period at a low force, since the actual tissue thickness is smaller for the high force situation compared to the low force situation.

The correlation increases the signal to noise ratio of the measured returning pulse period, providing an accurate measure of the tissue thickness.

There is provided according to embodiments of the invention a method, which is carried out by inserting a catheter into contact with a wall of a cavity in a body of a subject. The distal segment of the catheter is provided with a contact force sensor and an ultrasound transducer. The method is further carried out by actuating the transducer to acquire ultrasound reflection data from the wall of the cavity, and while the transducer is actuated, reciprocating the catheter against the wall of the cavity and measuring the contact force between the catheter and the wall of the cavity. The method is further carried out by correlating the reflection data with the contact force, identifying a set of the correlated reflection data that has the highest correlation with the contact force, determining a tissue thickness between the inner surface and the identified set of the reflection data according to times-of-flight therebetween.

An aspect of the method includes ablating the wall of the cavity responsively to the tissue thickness.

According to one aspect of the method, the transducer operated in M-mode.

According to a further aspect of the method, the catheter is reciprocated normal to the inner surface of the wall.

According to yet another aspect of the method, the cavity is a chamber of a heart of the subject and a cyclic movement of the heart urges the catheter into a reciprocal motion.

According to still another aspect of the method, reciprocating the catheter is performed by an actuator that is linked to the catheter.

An additional aspect of the method includes synchronizing the actuator with a cyclic movement of the heart.

Another aspect of the method includes regulating the impulse power of the actuator according to the intracardiac fluid pressure.

According to one aspect of the method, reciprocating the catheter is performed with sufficient force to compress the wall of the cavity by 0.3-0.5 mm.

According to another aspect of the method, reciprocating the catheter is performed at frequencies of 1-10 Hz.

There is further provided according to embodiments of the invention an apparatus, including a catheter configured for insertion into contact with a wall of a body cavity. A contact force sensor and an ultrasound transducer are disposed in the distal segment of the catheter. The apparatus includes an ultrasound generator operative for actuating the transducer to acquire ultrasound reflection data from the wall of the cavity, and an actuator operative for reciprocating the catheter against the wall of the cavity while the transducer is active. Electrical circuitry linked to the contact force sensor is operative for measuring contact force between the catheter and the wall of the cavity. A processor linked to the electrical circuitry and the transducer receives the reflection data. The processor is operative for identifying a set of the correlated reflection data that has the highest correlation with the contact force and for determining a tissue thickness between the inner surface and the identified set of the reflection data according to times-of-flight therebetween.

According to an aspect of the apparatus, an ablator is operative for ablating the wall of the cavity, the ablator being adjustable responsively to the tissue thickness.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

Definitions

Relevant modes of ultrasound imaging include:

A-mode (amplitude mode). An ultrasound transducer scans along a line and echoes are displayed as a function of their distances from the transducer.

B-mode (2-dimensional mode). An array of ultrasound transducers scan a plane through the body. Reflections are displayed as a 2-dimensional image.

M-mode (Motion mode). A pulsed mode in which the ultrasound transducer can be operated to produce an A-mode or a B-mode image. The display comprises a series of frames in which motion of a structure may be discerned.

Additionally, the transducer may be operated in a harmonic mode or may use pulse inversion. Such modes tend to produce clear data, which assist the correlations that are described below.

Figure 1:
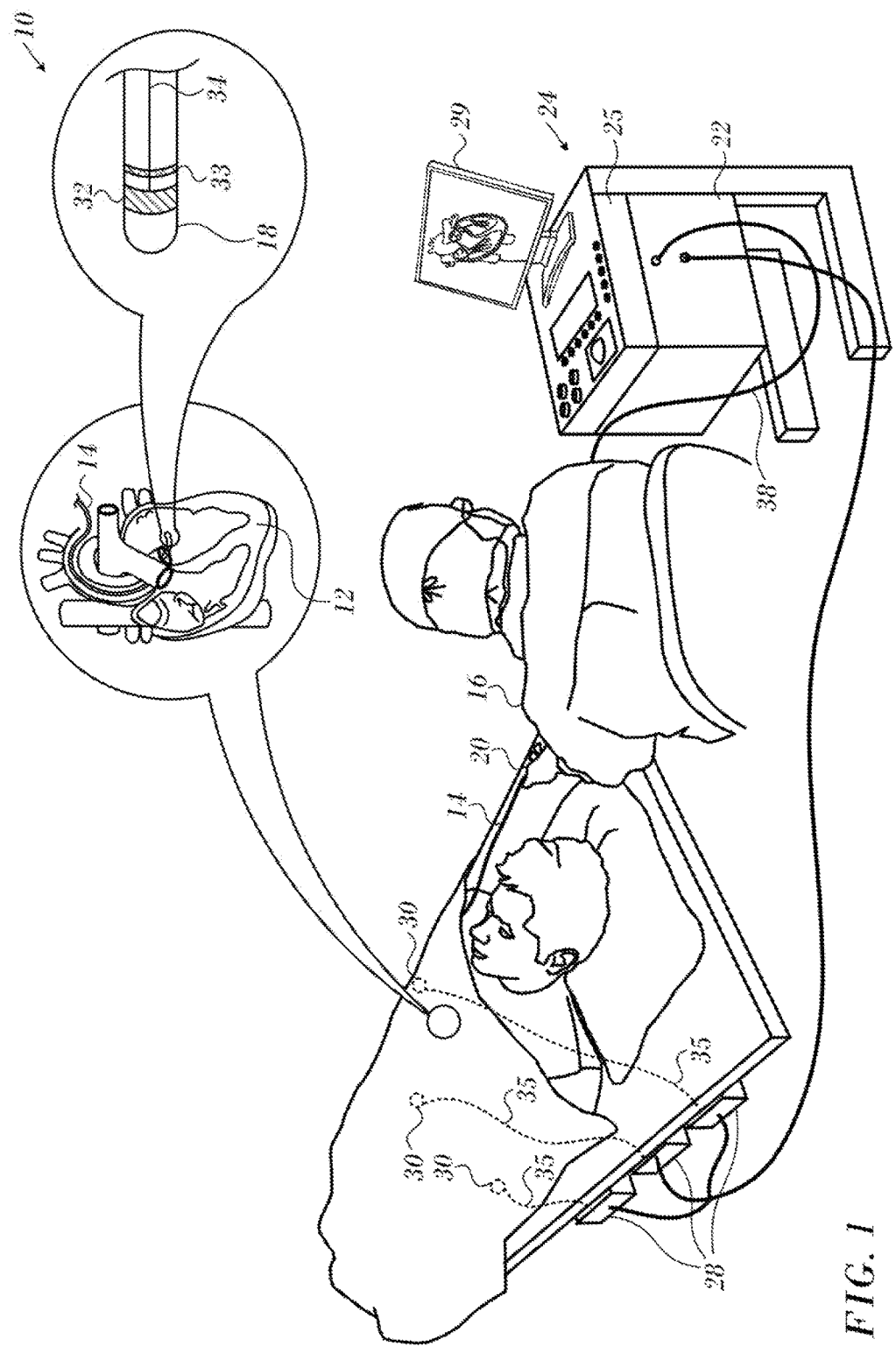
FIG. 1 is a pictorial illustration of a system for performing catheterization procedures on a heart, in accordance with a disclosed embodiment of the invention.

Turning now to the drawings, reference is initially made to FIG. 1, which is a pictorial illustration of a system 10 for evaluating electrical activity and performing diagnostic and therapeutic procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically above 60° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et ado, which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

In order to generate electroanatomic maps, the processor 22 typically comprises an electroanatomic map generator, an image registration program, an image or data analysis program and a graphical user interface configured to present graphical information on the monitor 29.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images.

Figure 2:
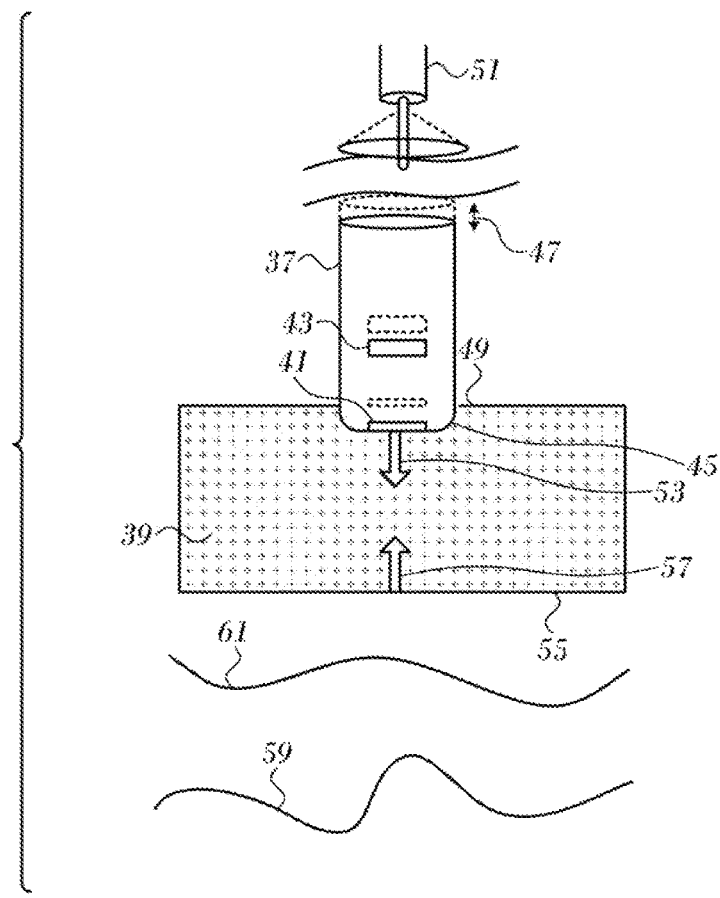
FIG. 2 is a schematic view of the distal portion of a catheter in contact with tissue being evaluated, in accordance with an embodiment of the invention.

Reference is now made to FIG. 2, which is a schematic view of the distal portion of a catheter 37 in contact with tissue 39 being evaluated, in accordance with an embodiment of the invention. An ultrasound transducer 41 is placed in the catheter 37, and contact force sensor 43 is disposed at or near distal tip 45. The catheter 37 reciprocates in a direction 47 that is generally normal to tissue surface 49, thereby compressing and decompressing at least the region of the tissue 39 that is immediately beneath the tip 45. The excursions of the catheter 37 occur at frequencies of 1-10 Hz and are performed with sufficient force to compress the tissue 39 by 0.3-0.5 mm, and as much as 5 mm. Reciprocation of the catheter 37 may be driven by a mechanical actuator 51. The practical range of time of flight reflections may be bounded according to the chamber in which the catheter 37 is found in order to increase the sensitivity of the algorithm. For example, the possible range of time of flight for a reflection for the right atrium would correspond to a tissue thickness of 0.25-7 mm and is considerably less than the full range of the ultrasound transducer or those needed to evaluate the left ventricle. In the left ventricle the possible range of time-of-flight for a reflection would correspond to a tissue thickness of 2-20 mm.

Suitable sensors for the contact force sensor 43 are described in commonly assigned U.S. Patent Application Publication Nos. 2012/0259194 and 2014/0100563, which are herein incorporated by reference.

The ultrasound transducer 41 may be a known single crystal type that emits efferent ultrasound pulses 53 in M-mode at a typical rate of 10 MHz. The pulses 53 reflect from tissue interface 55 and are then detected as afferent pulses 57. The tissue 39 may be the wall of a heart chamber, and the tissue interface 55 the overlying epicardium. The time-of-flight of the pulses 53, 57 vary as the tip 45 approaches and recedes from the tissue interface 55.

Other reflections may also be detected by the ultrasound transducer 41. These are exemplified in FIG. 2 by reflective interfaces 59, 61. The variations in the times-of-flight respectively associated with the interfaces 59, 61 correlate less well with the contact force as well as the motion of the catheter 37 than does the time-of-flight associated with the tissue interface 55. The tissue interface 55 can be identified among candidate reflections as having a time-of-flight with the highest correlation with the motion of the catheter 37.

Figure 3:
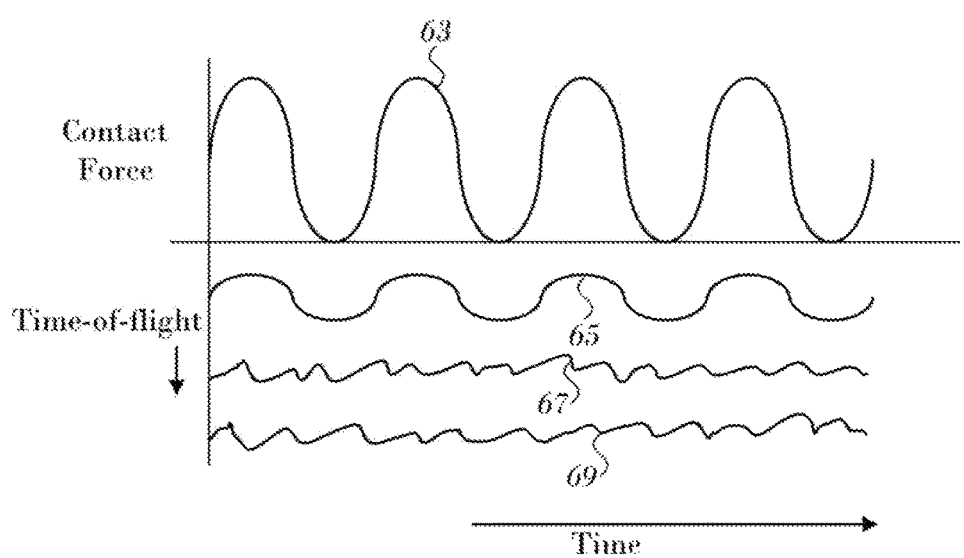
FIG. 3 is a graph showing correlation between contact force of a catheter tip and times-of-flight to tissue interfaces in accordance with an embodiment of the invention.

Reference is now made to FIG. 3, which is a prospective graphical example of correlation between contact force of a catheter tip and motion of the tissue interfaces, as indicated by times-of-flight using an ultrasound transducer, in accordance with an embodiment of the invention. Tracing 63 represents translational motion of the catheter tip perpendicular to a tissue surface. Tracings 65, 67, 69 represent times-of-flight associated with tissue interfaces 55, 59, 61 (FIG. 2). It is evident from inspection that the morphology of tracing 65 correlates well with that of tracing 63, while tracings 67, 69 appear to be uncorrelated with tracing 63. This may be confirmed using a standard correlation formula, e.g.:

$$\rho_{X,Y} = \operatorname{corr}(X, Y) = \frac{\operatorname{cov}(X, Y)}{\sigma_X \sigma_Y} = \frac{E[(X - \mu_X)(Y - \mu_Y)]}{\sigma_X \sigma_Y},$$

where for two random variables X, Y: μX and μY are expected values; $\sigma_X$ and $\sigma_Y$ are standard deviations; and $\rho_{X,Y}$ and corr(X, Y) are alternative notations for their correlation coefficient. Typically, the computations are applied to the last two seconds of the tracing. However, this interval is not critical. Based on the correlations, it may be concluded from tracing 65 that tissue interface 55 is most likely to correspond to the far wall of the tissue 39, and that interfaces 59, 61 are less likely to correspond to the far wall.

Figure 4:
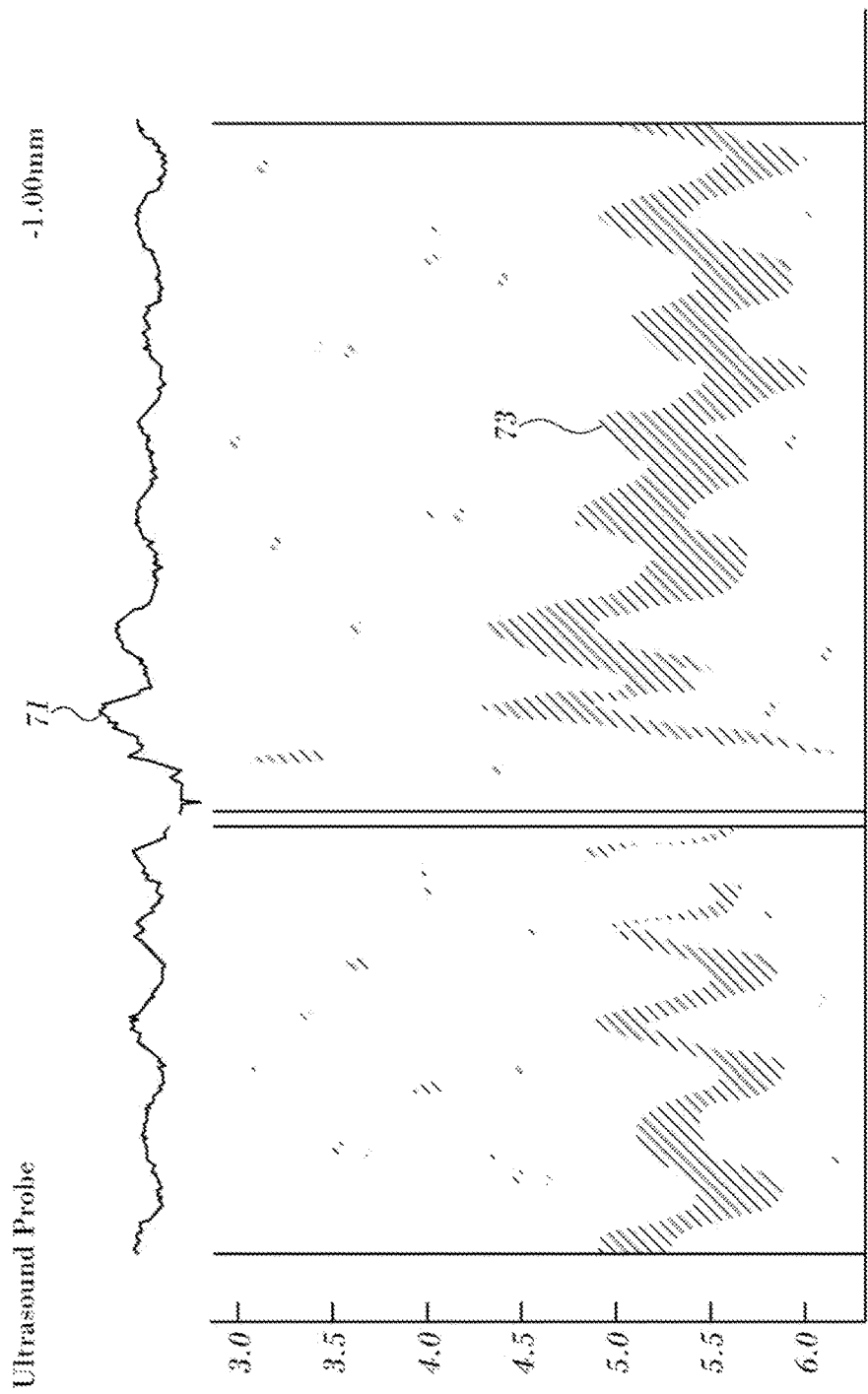
FIG. 4 is a graph showing correlation between contact force of a catheter tip and times-of-flight to tissue interfaces in accordance with an embodiment of the invention.

Reference is now made to FIG. 4, which is a graphical presentation similar to FIG. 3, in accordance with an embodiment of the invention. Contact force of the ultrasound probe operating in M-mode is indicated by tracing 71. Reflections have processed to determine their respective statistical correlations with the tracing 71, and been emphasized or de-emphasized according to their respective correlations with the tracing 71. Tracing 73, which has a relatively high correlation with the tracing 71, has been widened for emphasis, enabling the operator to readily distinguish it from other reflections. Other reflections have been de-emphasized.

Alternate Embodiment

This embodiment is similar to the previous embodiment, except now reliance is place in whole or in part on the cyclic motion of the heart, which when in contact with the catheter, creates a varying contact force, because the catheter resists displacement when it is urged in a centripetal direction as the heart contracts.

Referring again to FIG. 2, when the functional capacity of the heart is near normal, the motion of the tissue 39 itself is sufficient to produce reliable data, and the actuator 51 may be omitted or disabled. However, in cases of diminished regional or global functional capacity, e.g., congestive heart failure or certain arrhythmias, it may be necessary to augment the heart motion with the actuator 51 in order to generate sufficiently cyclical contact force with the catheter 37. In such case the actuator 51 may be synchronized with the heart motion and may be operated at reduced impulse power using a suitable controller (not shown) or the processor 22 (FIG. 1). For example, the timing of the actuator may be synchronized with an electrocardiographic signal and its impulse power dynamically controlled, e.g., by the processor 22 according to intracardiac pressure dynamics obtained from reading pressure sensors (not shown) in the catheter 37.

Operation.

Figure 5:
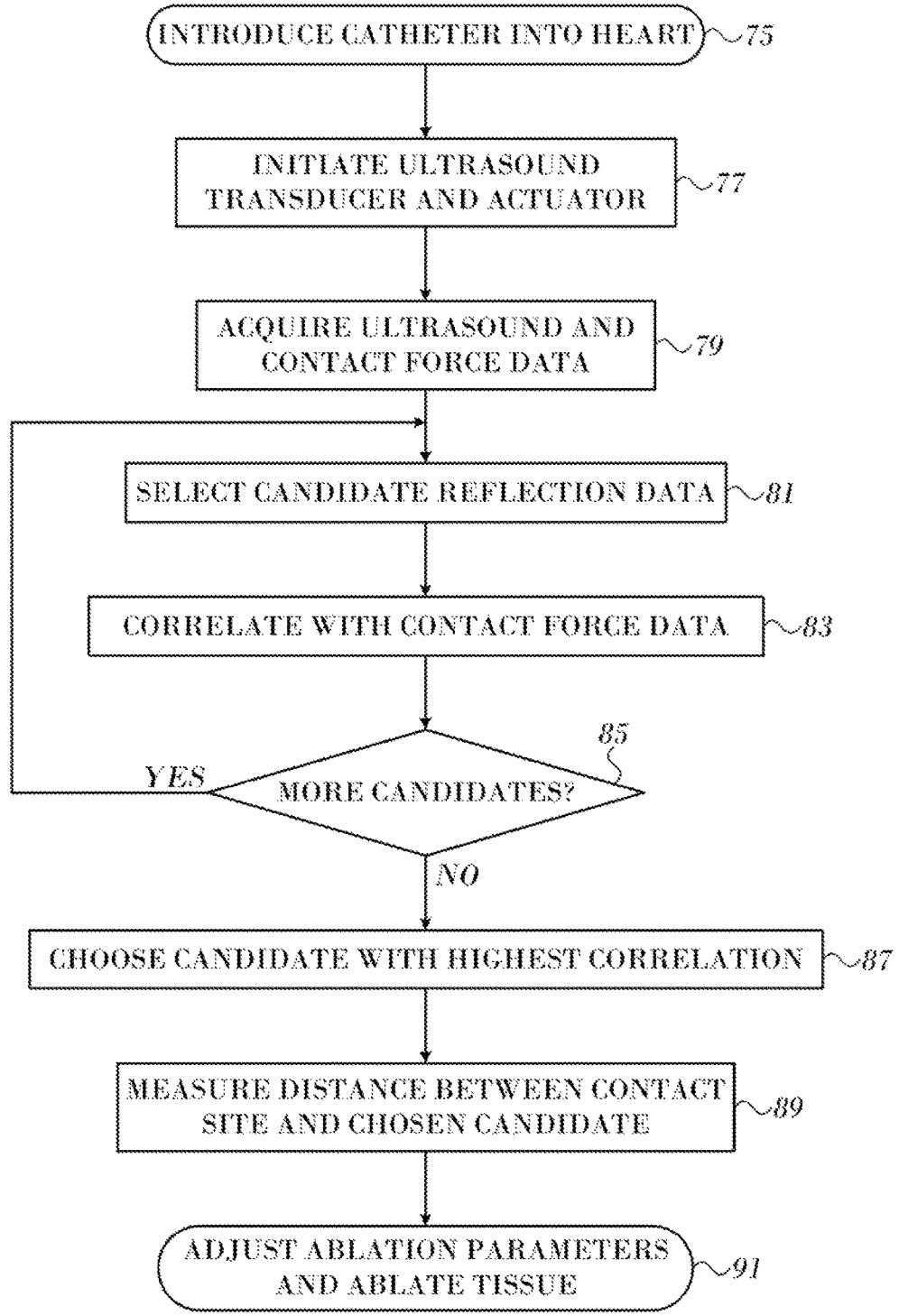
FIG. 5 is a flow-chart of a method of determining tissue thickness using ultrasound and force measurements in accordance with an embodiment of the invention.

Reference is now made to FIG. 5, which is a flow-chart of a method of determining tissue thickness using ultrasound and force measurements in accordance with an embodiment of the invention. The process steps are shown in a particular linear sequence for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At initial step 75 catheterization of a cardiac chamber is accomplished conventionally. A cardiac catheter having a contact force sensor and an ultrasound transducer at or near its tip is introduced into a cardiac chamber in contact with a target site of interest. Typically, the target site is the endocardial surface of the chamber and is subject to ablation. The catheter is generally provided with an ablation electrode for use with a control mechanism, for example components of the system 10 (FIG. 1).

Next, at step 77 the ultrasound transducer and an actuator are actuated to reciprocate the catheter against the target tissue as described above. The transducer is typically operated in M-mode.

Next, at step 79 ultrasound data are acquired while the catheter is in reciprocal motion, typically for about 2 sec. The contact force applied by the actuator is recorded during the image acquisition.

Next, at step 81 a candidate reflection data, e.g., an interface line is identified and selected from the image data that was acquired in step 79. This may be performed automatically by a suitably performed processor.

Next, at step 83, the data selected in step 81 is correlated with the contact force data that was acquired in step 79. As noted above, any suitable method of correlation may be applied in step 83.

Next, at decision step 85, it is determined if more candidate data remain to be evaluated. If the determination is affirmative, then control returns to step 81 to for another iteration.

If the determination at decision step 85 is negative, then control proceeds to step 87, the candidate having the greatest correlation with the contact force data is selected among the candidates. The chosen candidate is treated identifying the outer wall, i.e., the epicardial surface of the cardiac chamber.

Next, at step 89 the distance between the site of contact at the endocardial surface of the chamber and the chosen candidate is measured using conventional ultrasound techniques, e.g., by determining the appropriate time-of-flight. This distance is the tissue thickness at the point of contact with the catheter.

Then, at final step 91 ablation parameters, e.g., generator power and duration are set according to the tissue thickness that was measured in step 89 and the ablation electrode actuated to perform the desired therapeutic procedure.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
   inserting a catheter having a distal segment into contact with a wall of a cavity in a body of a subject, the cavity having an inner surface and an outer surface; the distal segment of the catheter being provided with a contact force sensor and an ultrasound transducer;

actuating the transducer to simultaneously acquire ultrasound reflection data associated with various tissue interfaces including from the wall of the cavity, the reflection data representative of times-of-flight from the various tissue interfaces during a given time;

while the transducer is actuated, reciprocating the catheter against the wall of the cavity a plurality of times during the given time and measuring a contact force between the catheter and the wall of the cavity to obtain contact force data over the given time;

comparing the reflection data with the contact force data over the given time;

identifying a set of the reflection data having a highest correlation with the contact force data over the given time; and determining a tissue thickness for the tissue interface associated with the identified set of the reflection data according to times-of-flight therebetween.

2. The method according to claim 1, further comprising ablating the wall of the cavity responsively to the tissue thickness.

3. The method according to claim 1, wherein actuating the transducer is performed in M-mode.

4. The method according to claim 1, wherein reciprocating the catheter is performed normal to the inner surface.

5. The method according to claim 1, wherein the cavity is a chamber of a heart of the subject and wherein reciprocating the catheter is performed by a cyclic movement of the heart that urges the catheter into a reciprocal motion.

6. The method according to claim 1, wherein reciprocating the catheter is performed by an actuator that is linked to the catheter.

7. The method according to claim 6, further comprising synchronizing the actuator with a cyclic movement of a heart of the subject.

8. The method according to claim 6, further comprising regulating an impulse power of the actuator according to an intracardiac fluid pressure.

9. The method according to claim 1, wherein reciprocating the catheter is performed with sufficient force to compress the wall of the cavity by 0.3-0.5 mm.

10. The method according to claim 1, wherein reciprocating the catheter is performed at frequencies of 1-10 Hz.

11. An apparatus, comprising:
a catheter having a distal segment configured for insertion into contact with a wall of a cavity in a body of a subject, the cavity having an inner surface and an outer surface;
a contact force sensor and an ultrasound transducer disposed in the distal segment;
an ultrasound generator operatively connected to the catheter and configured for actuating the transducer to simultaneously generate ultrasound reflection data associated with various tissue interfaces, including from the wall of the cavity, the reflection data representative of times-of-flight from the various tissue interfaces during a time;
an actuator operatively connected to the catheter and configured for reciprocating the catheter against the wall of the cavity a plurality of times during the time while the transducer is active;
electrical circuitry linked to the contact force sensor and operative for measuring a contact force between the catheter and the wall of the cavity; and
a processor linked to the electrical circuitry and the transducer, the processor configured for (i) receiving the reflection data during the given time, (ii) comparing the reflection data with contact force data measured by the contact force sensor during the time, (iii) identifying a set of the reflection data having a highest correlation with the contact force data during the time, and (iv) determining a tissue thickness for the tissue interface associated with the identified set of the reflection data according to times-of-flight therebetween.

12. The apparatus according to claim 11, further comprising an ablator operative for ablating the wall of the cavity, the ablator being adjustable responsively to the tissue thickness.

13. The apparatus according to claim 11, wherein the ultrasound generator is operative for actuating the transducer in M-mode.

14. The apparatus according to claim 11, wherein the actuator is operative for reciprocating the catheter normal to the inner surface.

15. The apparatus according to claim 11, wherein the actuator is operative for reciprocating the catheter with sufficient force to compress the wall of the cavity by 0.3-0.5 mm.

16. The apparatus according to claim 11, wherein the actuator is operative for reciprocating the catheter is performed at frequencies of 1-10 Hz.

\* \* \* \* \*